United States Patent [19]

Baird et al.

[11] Patent Number: 4,523,456
[45] Date of Patent: Jun. 18, 1985

[54] DETERMINATION OF SURFACE AND INTERFACIAL TENSION

[75] Inventors: Malcolm H. I. Baird, Dundas; Inderjit Nirdosh, Thunder Bay, both of Canada

[73] Assignee: University of Waterloo, Waterloo, Canada

[21] Appl. No.: 383,287

[22] Filed: May 28, 1982

[51] Int. Cl.³ ............................................. G01N 13/02
[52] U.S. Cl. ........................................... 73/64.4; 73/57
[58] Field of Search ..................................... 73/64.4, 57

[56] References Cited

U.S. PATENT DOCUMENTS 2,054,438  9/1936  Natelson ............................... 73/64.4
2,654,243 10/1953  Colthup et al. ........................ 73/64.4

Primary Examiner—Charles Frankfort
Assistant Examiner—David R. Schuster
Attorney, Agent, or Firm—Sim & McBurney

[57] ABSTRACT

The determination of the surface tension of a liquid or of the interfacial tension between two immiscible liquids is effected by drainage methods in which the movement of an air bubble or a droplet of the lighter liquid is observed, certain measurements made and the surface tension or interfacial tension determined from such measurments. The apparatus used, comprising a tapered tube, a rotating uniform diameter tube or a tilted uniform diameter tube, is simple and inexpensive and accurate measurements are obtained.

10 Claims, 3 Drawing Figures

DETERMINATION OF SURFACE AND INTERFACIAL TENSION

FIELD OF INVENTION

The present invention relates to the determination of surface and interfacial tension in liquids and to apparatus for use in such determination.

BACKGROUND TO THE INVENTION

The surface tension of a liquid and the interfacial tension between immiscible liquids are important thermodynamic properties. The most popular instrument used in practice is the tensiometer in which the force required to detach a ring or plate from an interface is measured. This technique is accurate but the equipment is expensive. Various other techniques have been patented, as set forth in U.S. Pat. Nos. 2,054,438, 2,654,243, 3,765,227 and 3,096,642, but none has been found to be entirely satisfactory.

SUMMARY OF INVENTION

In accordance with the present invention, there is provided a novel procedure for measuring surface tension and interfacial tension by drainage techniques in narrow elongate tubes. The drainage of a liquid from a narrow vertical tube which is open at the bottom but closed at the top is prevented when the capillary forces exceed the gravitational forces acting on the liquid meniscus. The critical tube diameter for prevention of drainage is a function of surface or interfacial tension, and this effect is utilized in this invention.

In the case of surface tension measurement, the movement of an air bubble through the continuous phase of liquid for which surface tension is to be measured is observed while in the case of the determination of interfacial tension the movement of a droplet of lighter liquid through a continuous phase of heavier liquid is observed. The tube in which the observation is made is made calibrated using liquids of known surface tension. Based on quantitative observations of bubble or droplet movement through the continuous phase towards an equilibrium point at which the bubble or droplet moves no further towards a closed end of the tube, the surface tension or interfacial tension is determined.

The procedure of determination of the surface tension or interfacial tension involves calculation thereof from the relationship:

$$\sigma = (\rho a d^2 / K)$$

wherein $\sigma$ is the surface tension or interfacial tension, $\rho$ is the density of the continuous phase, a is acceleration tending to move the bubble or droplet towards the closed end of the tube at the equilibrium point, d is the diameter of the tube at the equilibrium point and K is a calibration constant for the tube.

GENERAL DESCRIPTION OF INVENTION

The determination of surface tension or interfacial tension using the procedure of this invention may be effected in a number of different manners, three of which are specifically discussed below.

(a) Taper Tube Embodiment

Figure 1:
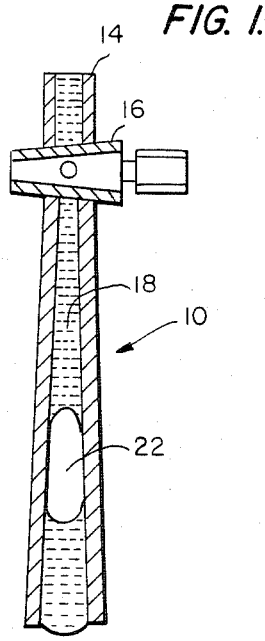
FIG. 1 is a sectional view of a tapered tube which may be used to effect a surface tension or interfacial tension determination in accordance with one embodiment of the invention.

In one embodiment of the invention as illustrated in FIG. 1, the rise of a bubble is allowed to take place in a narrow vertically upright tube 10 which has a linear taper from the lower end 12 thereof to the upper end 14 thereof and which is closable at its upper end, such as, by a stopcock 16 or the like.

In this embodiment, with the stopcock 16 open, the tube 10 first is filled with the test liquid or continuous phase 18 and then the stopcock 16 is closed. The liquid 18 is held within the tube and prevented from draining out by its surface tension which causes a drop 20 to form and be held at the lower open end of the tube.

The dispersed phase, which may take the form of air for surface tension measurement, or an immiscible lighter liquid for interfacial tension measurement, is injected into the base of the tube to form a bubble 22 or liquid droplet in the continuous phase. Typically, sufficient dispersed phase is injected into the base of the tube to form a cylindrical bubble 22 or droplet about 30 to 50 mm long. When two liquid phases are used, they usually are mutually saturated prior to effecting the procedure.

The bubble 22 or droplet rises gradually in the tapered tube, under the influence of capillary forces, with the continuous phase 18 draining down past it, until an equilibrium position is reached when the bubble or droplet can rise no higher in the tube as a result of a balance of the capillary and gravitational forces acting on the bubble or droplet.

For the purposes of calculating the surface tension or interfacial tension of the continuous phase liquid, the attainment of the equilibrium position may be awaited and the height of the nose of the bubble 22 or droplet above the lower end of the tube 10 measured, this measurement being used as a basis for determination of surface tension or interfacial tension. Alternatively, the rate of rise of the bubble 22 or droplet through the continuous phase 18 with time may be measured and this measurement used as a basis for determination of surface tension or interfacial tension.

Determination of the surface tension and interfacial tension is based on calculation from the equation:

$$\frac{\rho g d_o^2}{\sigma} = K \quad (1)$$

wherein $\sigma$ is the surface tension or interfacial tension, $\rho$ is the density of the liquid whose surface tension is measured or the difference in density between the liquids whose interfacial tension is measured, g is the gravitational force, $d_o$ is the critical tube diameter at which the bubble or droplet rises no further in the tube and K is a constant.

The constant K is a fixed value for the configuration of apparatus used in the determination and is arrived at by precalibration of the tapered tube using a liquid or liquids of known surface tension or interfacial tension values. For the liquid of known surface tension or the pair of immiscible liquids of known interfacial tension, the values of $\sigma$, $\rho$, $d_o$ and g are known, so that the values of the calibration constant (K) can be determined.

For a tested liquid of unknown surface tension or for two immiscible liquids of unknown interfacial tension, the appropriate values of $\rho$, g, $d_o$ and K are inserted in the unknown equation 1 and the $\sigma$ value thereby is determined.

The value of $d_o$ is obtained by direct observation or by calculation from the observed rate of rise of the bubble or droplet within the tube, as follows:

The rate of rise of the bubble or droplet is dictated by the rate at which the continuous phase can drain through a thin annular film near the tube wall and the thickness of this film is proportional to the difference between the tube diameter and the critical diameter for the tube.

Hence:

$$\delta = \frac{\phi(d - d_o)}{2} \quad (2)$$

wherein $\delta$ is the thickness of the film, d is the tube diameter at the point of determination of $\delta$, $d_o$ is the critical diameter and $\phi$ is a film thickness factor.

The flow rate of drainage as d approaches and approximates $d_o$ is governed by the relationship:

$$Q = \frac{\rho g \delta^3 (\pi d_o)}{3\mu} \quad (3)$$

wherein Q is the flow rate and $\mu$ is the viscosity of the draining liquid. The flow rate can also be calculated by continuity from the velocity of the bubble nose:

$$Q = \frac{\pi d_o^2}{4} \cdot \frac{dy}{dt} \quad (4)$$

It follows from equations (2) to (4) that the velocity of the bubble nose is governed by the relationship:

$$\frac{dy}{dt} = \frac{\rho g \phi^3}{6\mu d_o}(d - d_o)^3 \quad (5)$$

The critical diameter corresponds to an equilibrium vertical position $y_o$ in accordance with the relationship:

$$d_o = d_1 - \beta y_o \quad (6)$$

where $\beta$ is the angle of taper of the tube. Combining equations (5) and (6), a differential equation in y is obtained:

$$\frac{dy}{dt} = \frac{\rho g \beta^3 \phi^3}{6\mu d_o}(y_o - y)^3 \quad (7)$$

whence, by integration:

$$\frac{1}{(y_o - y)^2} = \frac{\rho g \beta^3 \phi^3 t}{3\mu d_o} + \text{constant} \quad (8)$$

The integration constant is assumed to be zero since at time zero the bubble nose is assumed to be distant from its equilibrium position. This simplification leads to the following simple rate expression:

$$y_o - y = \left(\frac{3\mu d_o}{\rho g \beta^3 \phi^3}\right)^{\frac{1}{2}} t^{-\frac{1}{2}} \quad (9)$$

Based on observation of the rate of rise of the bubble or droplet in a tapered tube of taper angle $\beta$, the surface tension or interfacial tension can be calculated. The value of $\phi$ can be determined using a liquid of known surface tension and is approximately 0.60 for air/liquid systems.

The technique for surface tension measurement using the tapered tube is very simple, in that, once the tube has been calibrated, the height of the meniscus of the bubble or droplet as a function of time is the only measured variable.

(b) Rotating Uniform Tube Embodiment

Figure 2:
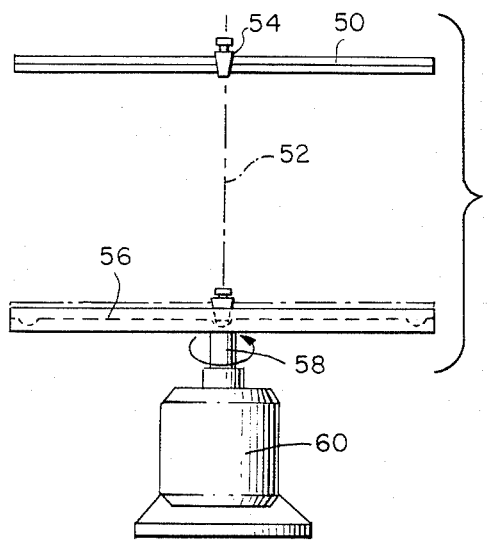
FIG. 2 is a perspective view of a rotating tube apparatus which may be used to effect a surface tension determination in accordance with a second embodiment of the invention.
Figure 3:
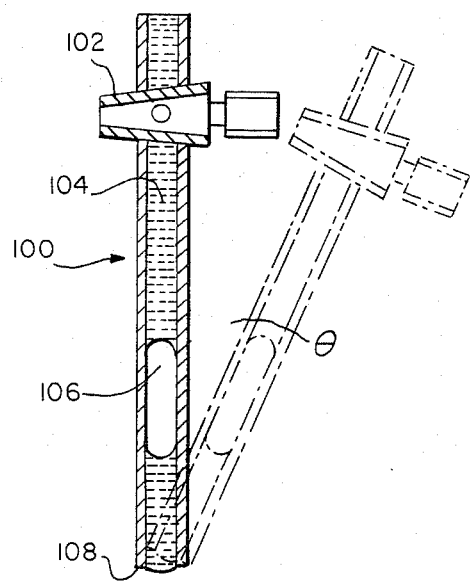
FIG. 3 is a sectional view of a uniform diameter tube which may be used to effect a surface tension or interfacial tension determination in accordance with a third embodiment of the invention.

In another embodiment of the invention, the determination is made in a horizontal tube 50 of uniform diameter which is rotated about a vertical axis extending through its mid-point as illustrated in FIG. 2. Any convenient diameter of tube may be used, typically about 1 to 3 mm. The tube 50 is provided with a closure member, such as a stopcock 54, at its centre. When the tube 50 is to be used for interfacial tension determination, the tube is also provided with closure members, such as stopcocks, at each end.

After filling the tube 50 with test liquid, the central stopcock 54 is closed, the tube 50 is mounted in a tube holder 56 which is mounted at its mid-point to the driven axle 58 of a motor 60, and the dispersed phase is injected into the open ends of the tube. When a liquid constitutes the dispersed phase, the end stopcocks (not shown) are then closed. The tube 50 is rotated about the vertical axis "by the motor 60" at a known speed of rotation (N) to cause the bubble or droplet to move axially within the tube towards the midpoint of the tube until an equilibrium is reached, when further rotation of the tube 50 fails to produce any further movement of the bubble or droplet towards the midpoint of the tube.

The distance ($R_o$) of the two bubbles or droplets from the centre of rotation of the tube 50 is measured and the two values averaged. The calculation of the surface tension or interfacial tension from the observed values is effected in analogous manner to that for the tapered tube embodiment. The relationship of equation 1 is expressed as follows for the rotating tube:

$$\frac{\rho(2\pi N)^2 R_o d^2}{\sigma} = K \quad (10)$$

wherein $\sigma$ is the surface tension or interfacial tension, $\rho$ is the density of the continuous phase in the case of surface tension measurement and the difference in density between the continuous and discontinuous phases in the case of interfacial tension measurement, N is the speed of rotation of the tube, $R_o$ is the critical radius from the centre of rotation, d is the diameter of the tube and K is a constant. The constant K is predetermined by calibration of the measurement tube using a continuous phase of known surface tension, taking into account the effect of gravity on the bubble in the tube.

Although the equipment used in this embodiment of the invention is more complex than that used in the tapered tube measurement, it avoids the need for a precision tapered tube and the measurement technique is simple, requiring only a measurement of the equilibrium radial position of the bubble or droplet, for a known tube diameter and rate of rotation of the tube.

(c) Tilted Uniform Tube Embodiment

A uniform diameter narrow bore tube 100 having a closure member, such as a stopcock 102, at the upper end thereof is used in this embodiment of the invention. The tube 100 is filled with continuous phase 104 and the stopcock 102 is closed. The discontinuous phase 106 is injected into the lower end 108 of the tube 100. The tube 100 is tilted to an angle at which the bubble 106 or droplet is just prevented from rising further in the tube 100 and the surface tension or interfacial tension is determined from this critical angle, based on the following considerations.

When a tube is tilted at an angle $\theta$ to the vertical, the component of gravity acting along the tube axis is g cos $\theta$, so that the surface tension or interfacial tension is determined, by analogy to equation 1, from the equation:

$$\frac{\rho g \cos\theta d_o^2}{\sigma} = K \quad (11)$$

The constant K is a function of $\theta$ and can be calibrated as a curve based on a known system. Hence there is a critical tilt angle $\theta_o$ below which a bubble is just prevented from rising through a continuous phase in a uniform tube whose diameter is slightly less than determined by the relationship:

$$d = \left(\frac{K_o \sigma}{g\rho}\right)^{\frac{1}{2}} \quad (12)$$

where $K_o$ is the K value at $\theta=0$.

In this embodiment of the invention, measurement of the critical angle $\theta_o$, for a uniform diameter calibrated tube, therefore, provides a measure of the surface tension or interfacial tension.

The apparatus which is used in this embodiment of the invention is very simple, requiring only a narrow bore uniform tube. Compared with the tapered tube and rotating tube embodiments, the measurement of bubble velocity as a function of angle tends to be somewhat tedious.

The present invention provides, therefore, a number of techniques to effect surface tension and interfacial tension measurement in a relatively simple and straightforward manner. The results obtainable using the invention have comparable accuracy to those obtained by conventional tensiometer measurement but are obtained at considerably lower cost.

EXAMPLES

EXAMPLE 1

A 40 cm length uniformly tapered tube having an inside diameter of 6 mm at the lower end and 2.5 mm at the upper end and equipped with a stopcock was used in surface tension and interfacial tension determinations. After filling the tube with the continuous phase and closing the stopcock, a small quantity of discontinuous phase was injected into the lower end of the tube to form a bubble (in the case of air) or a droplet (in the case of a lighter liquid) in the tube.

The rate of rise of the bubble or droplet was determined in each case and a plot of y vs. $t^{-\frac{1}{2}}$ was made in each case. A linear relationship was observed. The film thickness factor $\theta$ for the various systems was determined by slope analysis of the curves.

The results obtained for the parameters of equation (9) are reproduced in the following Table I:

TABLE I

| System (Temp.) | Properties | | | Results | | | |
|---|---|---|---|---|---|---|---|
| | $\rho$ (kg/m$^3$) | $\mu$ (mPa·s) | $\sigma$ (mN/m) | $y_o$ (mm) | $d_o$ (mm) | $\phi$ | K |
| Acetone/air (24° C.) | 782.9 | 0.33 | 23.7 | 355 | 2.89 | 0.62 | 2.77 |
| i.amyl alc./air (24° C.) | 804.7 | 3.9 | 23.73 | 351 | 2.935 | 0.61 | 2.83 |
| cyclohexane/air (24° C.) | 773.7 | 0.92 | 24.75 | 338 | 3.04 | 0.62 | 2.83 |
| methanol/air (24° C.) | 787.7 | 0.57 | 22.18 | 359 | 2.86 | 0.58 | 2.85 |
| methyl ethyl ketone/air (24° C.) | 800.1 | 0.42 | 24.2 | 348 | 2.95 | 0.60 | 2.82 |
| benzene/air (23° C.) | 875.6 | 0.62 | 28.46 | 335 | 3.07 | 0.58 | 2.85 |
| water/air (23° C.) | 996.6 | 0.97 | 72.13 | 156 | 4.63 | 0.56 | 2.91 |
| ethylene glycol/air (24° C.) | 1101.7 | 19 | 48.07 | 278 | 3.59 | 0.39 | 2.90 |
| ethylene glycol/benzene (24° C.) | 1087.8 / 886.0 | 12 / 0.57 | 7.92 | 318 | 3.22 | 0.40 | 2.85* |
| water/ethyl acetate (24° C.) | 996.2 / 900.4 | 0.97 / 0.48 | 6.89 | 164 | 4.57 | 0.34 | 2.85* |
| water/in amyl alc. (24° C.) | 995.6 / 822.7 | 0.97 / 3.9 | 4.50 | 372 | 2.75 | 0.25 | 2.85* |

*The K value is assumed in these cases because no exact value of $\sigma$ was available for these systems. The values of $\sigma$ given in column 3 have been calculated assuming K = 2.85 and these values compare quite favourably with the very limited data available in the literature.

As may be seen from the above results, for the liquid/air systems, the values of K have a relatively constant mean value of 2.85 and the value of the film thickness factor ($\phi$) is about 0.60.

EXAMPLE 2

A rotating tube apparatus was set up comprising a tube arranged horizontally for rotation about a vertical axis bisecting the length of the tube. The tube was filled with continuous phase and a central stopcock closed. A small (1 to 2 cm) air bubble or liquid droplet was injected into the open ends of the tube. For the experiments using liquid droplets, the tube was provided with stopcocks at both ends, which were closed after injection of the droplets into the tube ends.

The tube was rotated for about 20 minutes to cause the bubble or droplet to move towards the axis of rotation and to achieve an equilibrium position. Once rotation was completed, the distance of the nose of each bubble or droplet from the centre of rotation was measured and averaged.

The tube was calibrated using a number of systems for which surface tension and density data was available so as to establish a calibration curve of K vs. tan $\theta$, where $\theta$ is the resultant angle for the forces of gravity and rotation acting on the bubble or droplet.

Once calibration was completed, the apparatus was used on other systems, and the results for the parameters of equation (10) are reproduced in the following Table II:

of the liquid/liquid systems, in view of the paucity of literature values available.

EXAMPLE 3

A uniform bore tube of 3.95 mm diameter having a stopcock at the upper end thereof was filled with a 10% solution of methanol in water, the stopcock was closed and a bubble of air was injected into the lower end of the tube. The velocity of rise of the bubble within the tube was determined as a function of tilt angle and the surface tension calculated from equation (11), with the value of K being determined from the calibration curve established in Example 2. The results are reproduced in the following Table III:

TABLE III

| Angle $\theta$ | Bubble Velocity (mm/h) | K | $\sigma$ mN/m |
|---|---|---|---|
| 19° | 14.8 | 2.30 | 61.9 |
| 17° | 4.0 | 2.39 | 60.2 |
| 15° | 1.2 | 2.48 | 58.7 |
| | | | 59.0 Literature |

SUMMARY OF DISCLOSURE

In summary of this disclosure, the present invention

TABLE II

| System (Temp.) | N (r/s) | R cm | $\frac{g}{(2\pi N)^2 R}$ | K* | $\rho$ kg/m³ | $\sigma$ mN/m (obsd.) | $\sigma$ mN/m (Lit.) |
|---|---|---|---|---|---|---|---|
| (a) Tube dia. = 1.201 mm | | | | | | | |
| Acetone/air | 3.667 | 10.05 | 0.1833 | 2.630 | 785 | 22.97 | 23.04 |
| (24.8° C.) | 5.167 | 5.00 | 0.1866 | 2.625 | | 22.73 | |
| Toluene/Air | 4.117 | 9.25 | 0.1585 | 2.715 | 867 | 28.50 | 28.4 |
| (24° C.) | 5.033 | 5.93 | 0.1655 | 2.685 | | 27.54 | |
| 94.8 wt. % EtOH/H₂O/Air | 4.300 | 7.35 | 0.1828 | 2.630 | 790 | 23.25 | 22.72 |
| (24° C.) | 5.133 | 5.10 | 0.1848 | 2.625 | | 23.03 | |
| 54.2 wt. % EtOH/H₂O/Air | 4.933 | 6.05 | 0.1688 | 2.680 | 901 | 28.18 | 27.80 |
| (24° C.) | 5.400 | 5.00 | 0.1704 | 2.665 | | 28.06 | |
| 28.9 wt. % EtOH/H₂O/Air | 4.933 | 7.03 | 0.1453 | 2.760 | 951 | 33.53 | 32.90 |
| (24° C.) | | | | | | | |
| Heptane/Air | 5.000 | 5.40 | 0.1841 | 2.625 | 691 | 20.30 | 19.74 |
| (24° C.) | 5.633 | 4.20 | 0.1864 | 2.625 | | 19.97 | |
| Carbon tetrachloride/Air | 3.500 | 5.28 | 0.3845 | 2.155 | 1586 | 27.09 | 26.55 |
| (24° C.) | 4.017 | 4.00 | 0.3851 | 2.155 | | 27.05 | |
| i-Propanol/air | 4.983 | 5.00 | 0.2001 | 2.590 | 785 | 21.42 | 21.0 |
| (24° C.) | | | | | | | |
| (b) Tube dia. = 1.208 mm | | | | | $\Delta\rho$ | | |
| Water/n-butanol | 2.800 | 5.75 | 0.5511 | 1.90 | 144 | 1.97 | 1.8 |
| (21° C.) | 3.333 | 3.90 | 0.5734 | 1.88 | | 1.91 | (Temp. unknown) |
| | 3.267 | 4.15 | 0.5611 | 1.89 | | 1.97 | |
| | 2.967 | 5.00 | 0.5649 | 1.89 | | 1.93 | |
| Water/i-amyl alc. | 3.633 | 11.05 | 0.1703 | 2.70 | 170.4 | 5.30 | 5.0 |
| (21° C.) | 4.233 | 7.95 | 0.1744 | 2.68 | | 5.22 | (18° C.) |
| | 4.433 | 7.03 | 0.1805 | 2.66 | | 5.10 | |
| | 4.917 | 5.63 | 0.1819 | 2.66 | | 5.02 | |
| | 5.967 | 4.15 | 0.1682 | 2.70 | | 5.37 | |
| (c) Tube dia. = 2.538 mm | | | | | | | |
| Water/MIBK | 3.43 | 4.60 | 0.4583 | 2.08 | 193.3 | 12.79 | 9.7 |
| (21° C.) | 3.60 | 3.90 | 0.4916 | 2.02 | | 12.30 | (27.2° C.) |
| | 3.83 | 3.70 | 0.4555 | 2.09 | | 12.77 | 10.4 |
| | 4.30 | 2.90 | 0.4650 | 2.07 | | 12.73 | (29.3° C.) |
| Water/benzene | 7.33 | 6.20 | 0.0745 | 2.98 | 118.2 | 33.60 | 35.0 |
| (23° C.) | 8.17 | 4.85 | 0.0761 | 2.98 | | 32.65 | (20° C.) |
| | 8.75 | 4.25 | 0.0764 | 2.97 | | 32.93 | |

*K values are taken from calibration curve.

As may be seen from the results of the above Table II, for liquid/air systems, the determinations of surface tension were mostly within 1% of the literature data, while firm correlation was harder to obtain in the case provides a simple, inexpensive and accurate manner of determining the surface tension of a liquid or the interfacial tension between liquids utilizing drainage methods.

Modifications are possible within the scope of this invention.

What we claim is:

1. A method of determining the surface tension of a test liquid, which comprises:
   (a) calibrating a narrow elongate tube which has a bore which tapers uniformly from an open lower end to a closable upper end to determine a calibration constant (K) for that tube based on a liquid of known surface tension value by effecting the following sequence of steps (b) to (e) for said liquid of known surface tension value in place of the test liquid;
   (b) filling said tube with a continuous phase of the test liquid and closing the upper end of the tube to prevent the test liquid from draining from the lower open end of the tube;
   (c) injecting a bubble of air into the lower end of the tube;
   (d) permitting said bubble to rise under the influence of capillary forces to an equilibrium point above which the bubble does not rise as a result of a balance of gravitational and capillary forces thereon; and
   (e) calculating the surface tension of the test liquid from the relationship:

$$\sigma = \frac{\rho \, g \, d_o^2}{K} \quad (I)$$

wherein $\sigma$ is the surface tension of the test liquid, $\rho$ is the density of the test liquid, g is the gravitational constant, $d_o$ is the diameter of the tube at the equilibrium point and K is the calibration constant.

2. The method of claim 1 wherein $d_o$ is determined by measuring the distance of the upper extremity of the bubble from the lower end of the tube ($y_o$), and calculating the same from the relationship:

$$d_o = d_1 - \beta y_o$$

wherein $d_1$ is the diameter of the tube at the lower end and $\beta$ is the taper angle.

3. A method of determining the surface tension of a test liquid, which comprises:
   (a) calibrating a narrow elongate tube which has a bore which tapers uniformly from an open lower end to a closable upper end to determine a calibration constant (K) for that tube based on a liquid of known surface tension value by effecting the following sequence of steps (b) to (f) for said liquid of known surface tension value in place of the test liquid;
   (b) filling said tube with a continuous phase of the test liquid and closing the upper end of the tube to prevent the test liquid from draining from the lower open end of the tube;
   (c) injecting a bubble of air into the lower end of the tube;
   (d) permitting said bubble to rise under the influence f capillary forces towards an equilibrium point above which the bubble will not rise as a result of a balance of gravitational and capillary forces thereon;
   (e) calculating said equilibrium point by observing the rate of rise with time of the bubble within the tube, and using said rate of rise to calculate the equilibrium point; and
   (f) calculating the surface tension of the test liquid from the relationship;

$$\sigma = \frac{\rho \, g \, d_o^2}{K} \quad (I)$$

wherein $\sigma$ is the surface tension of the test liquid, $\rho$ is the density of the test liquid, g is the gravitational constant, $d_o$ is the diameter of the tube at the equilibrium point and K is the calibration constant.

4. A method of determining the surface tension of a test liquid, which comprises:
   (a) determining a calibration curve for a narrow elongate tube which has a bore of uniform diameter and is closable at its approximate midpoint and has open ends based on liquids of known surface tension value by effecting the following sequence of steps (b) to (h) for each of said liquid of known surface tension value in place of the test liquid and calibrating individual values of (K) for the liquids from equation (1) below for variables of the relationship:

$$\frac{g}{(2\pi N)^2 R_o}$$

wherein N and $R_o$ are as defined below for equation (1);
   (b) filling said tube with a continuous phase of the test liquid and closing the tube at its midpoint;
   (c) mounting said tube horizontally for rotation about a vertical axis extending through said approximate midpoint;
   (d) injecting a separate bubble of air into each open end of the tube;
   (e) rotating said tube about said vertical axis at a speed only sufficient to cause each said bubble to pass through the test liquid towards the approximate midpoint until an equilibrium point is reached beyond which continued rotation of said tube produces no further bubble movement;
   (f) ceasing rotation of said tube;
   (g) determining the distance of the equilibrium point from the approximate midpoint for each bubble and averaging the values obtained; and
   (h) calculating the surface tension of the test liquid from the relationship:

$$\sigma = \frac{\rho (2\pi N)^2 R_o d^2}{K} \quad (1)$$

wherein $\sigma$ is the surface tension of the test liquid, $\rho$ is the density of the test liquid, N is the number of revolutions per second of the tube, $R_o$ is the average distance of the equilibrium point from the centre of rotation, d is the diameter of the tube, and K is the calibration constant for the tube read from the calibration curve in accordance with the value of the relationship:

$$\frac{g}{(2\pi N)^2 R_o}$$

for the test liquid.

5. A method of determining the surface tension of a test liquid, which comprises:
(a) determining a calibration curve for a narrow elongate tube which has a bore of uniform diameter and is closable at its upper end by effecting the sequence of the following steps (b) to (f) for a liquid of known surface tension value and calibrating individual values of the calibration constant (K) from equation (1) below for variables of the tangent of angles of tilt (tan $\theta$) of the tube;
(b) filling said tube with the test liquid and closing the upper end of the tube to prevent the test liquid from draining from the lower open end of the tube;
(c) injecting a bubble of air into the lower end of the tube;
(d) permitting said bubble to rise in said tube;
(e) determining a critical angle of tilt of the tube ($\theta_o$) from the vertical at which the bubble is just prevented from rising further in the tube by observing the rate of rise of said bubble in the tube as a function of the angle of tilt ($\theta$) and using said rate of rise to calculate the critical angle; and
(f) calculating the surface tension of the test liquid from the relationship:

$$\sigma = \frac{\rho g\, d^2 \cos\theta_o}{K} \quad (\text{I})$$

wherein $\sigma$ is the surface tension of the test liquid, $\rho$ is the density of the test liquid, g is the gravitational constant, d is the diameter of the tube and K is the calibration constant of the tube for the critical angle ($\theta_o$) read from the calibration curve in accordance with the value of tan ($\theta_o$) for the test liquid.

6. A method of determining the interfacial tension between two immiscible test liquids, a first one of said test liquids having a lower density than a second one of said test liquids, which comprises:
(a) calibrating a narrow elongate tube which has a bore which tapers uniformly from an open lower end to a closable upper end to determine a calibration constant (K) for that tube based on two immiscible liquids of known interfacial tension value by effecting the following sequence of steps (b) to (e) for said two immiscible liquids of known interfacial tension value;
(b) filling said tube with a continuous phase of the second test liquid and closing the upper end of the tube to prevent the second test liquid from draining from the lower end of the tube;
(c) injecting a droplet of the first test liquid into the lower end of the tube;
(d) permitting said droplet to rise in said tube under the influence of capillary forces to an equilibrium point above which the droplet does not rise as a result of a balance of gravitational and capillary forces thereon;
(e) calculating the interfacial tension between the two test liquids from the relationship:

$$\sigma = \frac{\rho\, g\, d_o^2}{K} \quad (\text{I})$$

wherein $\sigma$ is the interfacial tension between the two test liquids, $\rho$ is the difference in density between the two liquids, g is the gravitational acceleration, $d_o$ is the diameter of the tube at the equilibrium point and K is the calibration constant.

7. The method of claim 6 wherein $d_o$ is determined by measuring the distance of the upper extremity of the droplet from the lower end of the tube ($y_o$), and calculating the same from the relationship:

$$d_o = d_1 - \beta y_o$$

wherein $d_1$ is the diameter of the tube at the lower end and $\beta$ is the taper angle.

8. A method of determining the interfacial tension between two immiscible test liquids, a first one of said test liquids having a lower density than a second one of said test liquids, which comprises:
(a) calibrating a narrow elongate tube which has a bore which tapers uniformly from an open lower end to a closable upper end to determine a calibration constant (K) for that tube based on two immiscible liquids of known interfacial tension value by effecting the following sequence of steps (b) to (f) for said two immiscible liquids of known interfacial tension value;
(b) filling said tube with a continuous phase of the second test liquid and closing the upper end of the tube to prevent the second test liquid from draining from the lower end of the tube;
(c) injecting a droplet of the first test liquid into the lower end of the tube;
(d) permitting said droplet to rise in said tube under the influence of capillary forces towards an equilibrium point above which the droplet will now rise as a result of a balance of gravitational and capillary forces thereon;
(e) calculating said equilibrium point by observing the rate of rise with time of the droplet within the tube, and using said rate of rise to calculate the equilibrium point; and
(f) calculating the interfacial tension between the two test liquids from the relationship:

$$\sigma = \frac{\rho\, g\, d_o^2}{K} \quad (\text{I})$$

wherein $\sigma$ is the interfacial tension between the two test liquids, $\rho$ is the difference in density between the two liquids, g is the gravitational acceleration, $d_o$ is the diameter of the tube at the equilibrium point and K is the calibration constant.

9. A method of determining the interfacial tension between two immiscible test liquids, a first of said test liquids having a lower density than a second one of said test liquids, which comprises:
(a) determining a calibration curve for a narrow elongate tube which has a bore of uniform diameter and is closable at its approximate midpoint and also at its ends based on pairs of liquids of known interfacial tension values by effecting the following sequence of steps (b) to (h) for each said pair of liquids of known interfacial value in place of the test liquids and calibrating the individual values of (K) for the pairs of liquids from equation (1) below for variables of the relationship:

$$\frac{g}{(2\pi N)^2 R_o}$$

wherein N and $R_o$ are as defined below for equation (1);

(b) filling said tube with a continuous phase of the second test liquid and closing the tube at its midpoint;

(c) mounting said tube horizontally for rotation about a vertical axis extending through said approximate midpoint;

(d) injecting a separate droplet of the first test liquid into each of the open ends of the tube and closing the ends of the tube;

(e) rotating said tube about said vertical axis at a speed only sufficient to cause each said droplet to pass through the second test liquid towards the approximate midpoint until an equilibrium point is reached beyond which continued rotation of said tube produces no further droplet movement;

(f) ceasing rotation of said tube;

(g) determining the distance of the equilibrium point from the approximate midpoint for each droplet and averaging the values obtained; and (h) calculating the interfacial tension between the two test liquids from the relationship:

$$\sigma = \frac{\rho(2\pi N)^2 R_o d^2}{K} \quad (1)$$

wherein $\sigma$ is the interfacial tension between the two test liquids, $\rho$ is the difference in density between the two liquids, N is the number of revolutions per second of the tube, $R_o$ is the average distance of the equilibrium point from the centre of rotation, d is the diameter of the tube, and K is the calibration constant for the tube read from the calibration curve in accordance with the value of the relationship:

$$\frac{g}{(2\pi N)^2 R_o}$$

for the two test liquids.

10. A method of determining the interfacial tension between two immiscible test liquids, a first of said test liquids having a lower density than a second one of said test liquids, which comprises:

(a) determining a calibration curve for a narrow elongate tube which has a bore of uniform diameter and is closable at its upper end by effecting the sequence of the following steps (b) to (f) for pairs of liquids of known interfacial tension value and calibrating individual values of the calibration constant (K) from equation (1) below for variables of tangent of angles of tilt ($\tan \theta$) of the tube;

(b) filling said tube with the second test liquid and closing the upper end of the tube to prevent the second test liquid from draining from the lower end of the tube;

(c) injecting a droplet of the first test liquid into the lower end of the tube;

(d) permitting said droplet to rise in said tube;

(e) determining a critical angle of tilt of the tube ($\theta_o$) from the vertical at which the droplet is just prevented from rising further in the tube by observing the rate of rise of said droplet in the tube as a function of the angle of tilt ($\theta$) and using said rate of rise to calculate the critical angle; and (f) calculating the interfacial tension between the two test liquids from the relationship:

$$\sigma = \frac{\rho g \, d^2 \cos\theta_o}{K} \quad (1)$$

wherein $\sigma$ is the interfacial tension between the two test liquids, $\rho$ is the difference in density between the two test liquids, g is the gravitational constant, d is the diameter of the tube and K is the calibration constant of the tube for the critical angle $\theta_o$ read from the calibration curve in accordance with the value of $\tan(\theta_o)$ for the two test liquids.

* * * * *